United States Patent
Hayashi et al.

[11] Patent Number: 5,357,117
[45] Date of Patent: Oct. 18, 1994

[54] METHOD OF MONITORING THE PRESENCE OR ABSENCE OF LIQUID AND APPARATUS THEREFOR

[75] Inventors: Hidechika Hayashi, Yokohama; Yukio Mitsuhisa, Sagamihara, both of Japan

[73] Assignee: Tosoh Corporation, Yamaguchi, Japan

[21] Appl. No.: 59,369

[22] Filed: May 12, 1993

[30] Foreign Application Priority Data

May 15, 1992 [JP] Japan .................................. 4-147903

[51] Int. Cl.$^5$ ............................................. G01N 15/06
[52] U.S. Cl. .................................... 250/573; 356/338; 222/66
[58] Field of Search ............... 250/573, 576, 577, 205; 356/338, 339, 440–442, 246; 604/65, 66; 222/66, 56

[56] References Cited

U.S. PATENT DOCUMENTS

| | | | |
|---|---|---|---|
| 4,038,982 | 8/1977 | Burke et al. | 250/573 |
| 4,644,755 | 2/1987 | Esslinger et al. | 62/126 |
| 4,794,806 | 1/1989 | Nicoli et al. | 250/576 |

FOREIGN PATENT DOCUMENTS

| | | |
|---|---|---|
| 2818264 | 11/1978 | Fed. Rep. of Germany . |
| 58-198761 | 11/1983 | Japan . |
| 62-091818 | 4/1987 | Japan . |

*Primary Examiner*—David C. Nelms
*Assistant Examiner*—Que T. Le
*Attorney, Agent, or Firm*—Sughrue, Mion, Zinn, Macpeak & Seas

[57] ABSTRACT

A method of monitoring a discharge of a liquid comprises the steps of: measuring a presence or absence of a liquid discharged at an optional area of a passage for the liquid during discharging the liquid of a vessel through the passage; comparing a measurement result obtained in said measuring step with a reference measurement result which are to be obtained when a discharge of the liquid is reliably carried out; and determining as to whether a discharge operation for the liquid has been reliably performed. And an apparatus for performing the method.

16 Claims, 8 Drawing Sheets

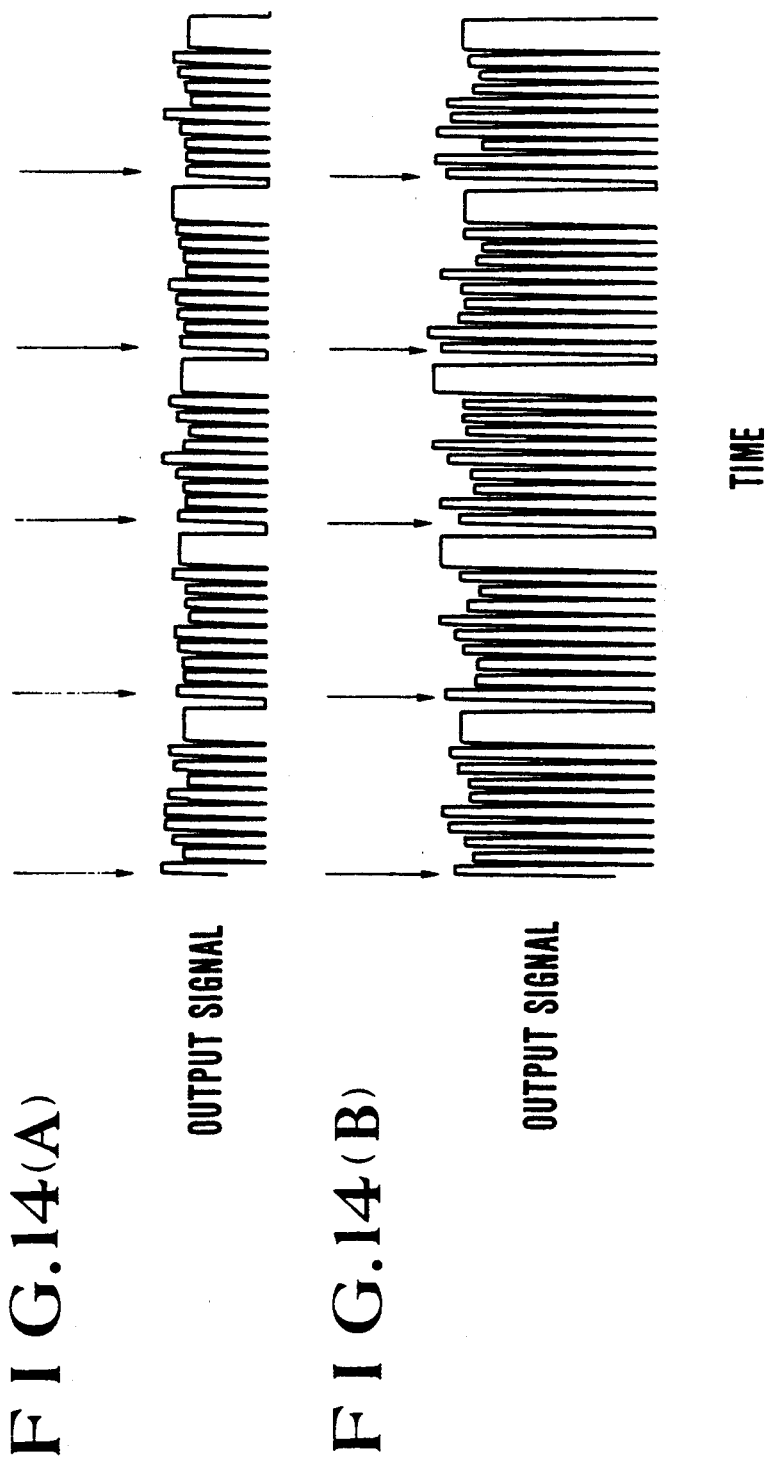

METHOD OF MONITORING THE PRESENCE OR ABSENCE OF LIQUID AND APPARATUS THEREFOR

BACKGROUND OF THE INVENTION

1. Field of the Invention

The present invention relates to a method of monitoring discharge of liquid, and more particularly to a method of detecting whether the discharge operation has been reliably carried out during the discharge of liquid from a vessel. The present invention also relates to an apparatus for practicing the method of monitoring the discharge of liquid.

2. Description of the Related Art

For example, in a biochemical analysis of which an immunoassay such as a heterogeneous immunoassay is representative, first, a sample, for example, a serum to be assayed, is injected into a reaction vessel which contains a solid phase carrying an antibody required for an immune reaction, a label antibody and the like to induce the immune reaction with an antigen in the sample, so that an immune reaction complex is formed on the solid phase. Subsequently, a washing operation referred to as a B(Bind)/F(Free) washing is carried out to remove a label antibody which does not contribute to the formation of the immune reaction complex, and finally the remaining label quantity is measured.

The washing operation referred to as the B/F washing includes the operation for discharging the liquid out of the vessel, and the operation for injecting a suitable washing solution, a reagent solution or the like into the vessel. The discharge operation is performed, for example, using a liquid discharge apparatus comprising a tube adapted to serve as a liquid discharge outlet and a passage as well, an end of which tube being connected directly or indirectly to a liquid suction force generator such as a negative pressure generator, in such a way that the end of the tube is penetrated into the liquid in the vessel. Consequently, it is usual for an automatic immunoassay apparatus or the like to equip a washing solution supply device and a liquid discharge apparatus between a sample/reagent injection apparatus and the measuring apparatus.

Also in a general chemical analysis, for example, in a case where the same reaction vessel is repeatedly used, the used vessel will be washed every use. This washing operation includes both the operation for injecting a washing solution into the vessel, and the operation for discharging a washing solution out of the vessel. It is usual for such an assay apparatus to equip a washing solution supply device and a liquid discharge apparatus after the measuring apparatus.

There is a need to provide the operation of exhausting a reaction solution from the reaction vessel, sometimes, for example, also in a case where the reaction solution is introduced from the reaction vessel to a flow cell for a measurement, other than the discharge operation for a liquid such as a washing solution as mentioned above.

For example, in the B/F washing in the automatic immunoassay apparatus, an incompleted discharge of liquid from a reaction vessel has a significant effect on the measurement result and also brings a danger such that the liquid in the reaction vessel overflows when a washing solution is injected into the reaction vessel. The overflow hinders the mechanical movement, corrodes the structure and causes the current leakage. Further, there is such a possibility that a biosample such as a blood serum as a sample contains the virus having an infectivity. Thus, the overflow of the liquid out of the vessel must be avoided as much as possible.

Further, for example, in the washing of a reaction vessel in the automatic chemical analysis apparatus, an incompleted discharge of liquid from the reaction vessel leaves the vessel as stained by the liquid and sometimes the vessel containing a residual washing solution is used for the next measurement. These would have a significant effect on the analysis result.

The following cases may be considered as a cause of an incompleted discharge of liquid from the reaction vessel. That is, as a first case, it is assumed that a tube, which constitutes a passage for a liquid flow of a liquid discharge apparatus, is bent or pinched and thus the passage is closed. As a second case, it is assumed that a suction force of a liquid suction force generator for leading the liquid from the reaction vessel to the discharge pass is weakened owing to an occurrence of any problems on the liquid suction force generator, so that the liquid is not led to the passage. And as third case, it is assumed that there occurs a clogging on an opening formed at one end of a liquid passage or a tube constituting the liquid passage, to be inserted into the liquid so that the passage has been substantially closed.

In order to keep the discharge operation for liquid in good order, according to the prior art, inspection of the liquid discharge apparatus is carried out regularly to keep it in a reliable state, and also even if it is in a good condition, parts used for a given period of time or a given number of times are replaced by new parts. Thus, these measures cope with unexpected situations. However, these countermeasures are not effective to prevent the clogging of the passage or the like which will happen suddenly. Hence, it is requested to provide a method of monitoring as to whether the discharge operation has been reliably performed during the discharge of liquid.

SUMMARY OF THE INVENTION

It is, therefore, an object of the present invention to provide a method of monitoring as to whether an operation for discharge of liquid out of a vessel has been reliably carried out, in an immunoassay, a chemical analysis and the like, and an apparatus for practicing the method of monitoring the liquid discharge operation.

The present invention has been made on the basis of a principle such that it is possible to monitor as to whether the liquid discharge operation has been reliably carried out by means of measuring the presence or absence of the liquid discharged at an optional area of the liquid passage, and comparing the thus obtained measurement result with a reference measurement result which is to be obtained when the discharge of liquid is reliably carried out. This principle has been found by the inventors of the present application.

To achieve the above-described object, according to one aspect of the present invention, there is provided a method of monitoring the discharge of liquid, comprising the steps of: measuring the presence or absence of the liquid discharged at an optional area of the liquid passage during discharging the liquid from a vessel through the passage; comparing the measurement result obtained in said measuring step with a reference measurement result which is to be obtained when the discharge of the liquid is reliably carried out; and determining as to whether the discharge operation for the liquid has been reliably performed.

It is another object of the present invention to provide an apparatus for monitoring the discharge of liquid comprising: a liquid passage for forming a discharge outlet for the liquid, at least one end of the liquid passage being connected directly or indirectly to liquid suction force generator means, and another end thereof being connected to a vessel; and a liquid measuring means provided on said liquid passage for measuring the presence or absence of the liquid discharged at an optional area of said liquid passage.

The objects, features and advantages of the present invention will become more apparent from the following detailed description of preferred embodiments of the present invention, taken in conjunction with the accompanying drawings.

BRIEF DESCRIPTION OF THE DRAWING

FIG. 1(a) is a graph showing a relation between an integrated value of the time (vertical axis) and the time elapsed (axis of abscissa), and FIG. 1(b) is a graph showing a relation between an output signal (vertical axis) from a liquid measuring unit and the time elapsed (axis of abscissa).

FIG. 2(a) and FIG. 2(b) are graphs showing the corresponding matters as in FIG. 1(a) and FIG. 1(b), respectively.

FIG. 3(a) and FIG. 3(b) are graphs showing the corresponding matters as in FIG. 1(a) and FIG. 1(b), respectively.

FIG. 4(a) and FIG. 4(b) are graphs showing the corresponding matters as in FIG. 1(a) and FIG. 1(b), respectively.

FIG. 5(a) and FIG. 5(b) are graphs showing the corresponding matters as in FIG. 1(a) and FIG. 1(b), respectively.

FIG. 6(a) and FIG. 6(b) are graphs showing the corresponding matters as in FIG. 1(a) and FIG. 1(b), respectively.

FIG. 7(a) and FIG. 7(b) are graphs showing the corresponding matters as in FIG. 1(a) and FIG. 1(b), respectively.

FIG. 14(A) and FIG. 14(B) are chart plotting an output signal of a liquid measuring unit (graph shown in part (A) of FIG. 14) in the event that the liquid discharge operation is reliably performed and an output signal of the liquid measuring unit (graph shown in part (B) of FIG. 14) in the event that the liquid discharge operation is defective, in which axis of abscissa denoted time elapsed. In accordance with the chart of FIG. 14, when the liquid discharge operation is performed ten times, it is treated as one set, and five sets of result are shown in the respectively events. An initial operation of the respective sets is marked with an arrow.

DETAILED DESCRIPTION OF THE PREFERRED EMBODIMENT

Figure 1A:
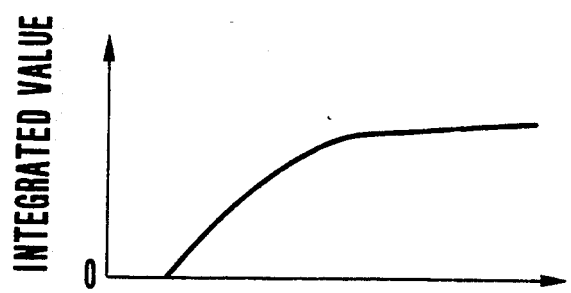
FIG. 1(a) and FIG. 1(b) show measurement results on a two dimensional basis in a case where a discharge operation is reliably performed, and particularly.

As vessels V for use in operations for assay, measurement, analysis or the like, there are known, for example, a cap type provided with a top-opening, a box type, etc. Any of these types of vessel can be applicable to the present invention. For example, the cap type of vessel permits a mechanical insertion of a B (Bind)/F (Free) washing apparatus or probe W etc. for a liquid discharge into the liquid passage through the top-opening thereof. If the box type of vessel is used, formation of an aperture near the bottom will permit a suitable tube as a liquid passage to be connected with the formed aperture. In the latter, it may be preferably to provide such an arrangement that the aperture is able to be closed, while no discharge is required, so as to prevent the liquid in the vessel from being naturally discharged through the liquid passage. In this manner it is rendered possible to arrange the passage for a liquid discharge even in any types of vessel, and thus it is possible to monitor the liquid discharge by performing a measurement as set forth below through such a passage.

The liquid passage 2 is for leading the discharged liquid to an arbitrary place, for example, a liquid pool for the discharged liquid, and a flow cell for measurement. Usually, the tube-like shaped passage is used as the liquid passage 2, but it is not confined to this type of passage. The liquid passage may be used, one end of which is connected directly or indirectly to a liquid suction force generator 12, and the other end being adapted to form a liquid discharge outlet 0. The liquid suction force generator 12 is, for example, a vacuum pump for generating a negative pressure. By way of example where the one end of the liquid passage is connected directly to the liquid suction force generator, there is, for example, such a case that the liquid suction force generator is a peristaltic pump, and the liquid passage is a silicon pipe. By way of example where the one end of the liquid passage is connected indirectly to the liquid suction force generator 12 (see FIG. 10), there is, for example, such a case that a vacuum pump as the liquid suction force generator 12 is connected via a tube 13 to a bottle 20 for trapping the discharged liquid (e.g., Japanese Patent Application No. Sho. 62-227755) or the like, and the liquid passage 2 is connected to this bottle 20 or the liquid pool.

The other end of the liquid passage forms a liquid discharge outlet. The liquid passage may be constructed with not only uniform material and shape in its entirety, but also mutually different kinds of material and mutually different shapes of member. By way of example when only the liquid discharge outlet is constructed with a configuration or a member preferable for a liquid discharge, the discharge outlet may be constructed with a looseness of a filter member so as to prevent a carrier, which carries an antibody or the like, for example, in a heterogeneous immunoassay reaction, from penetrating into the liquid passage. Further, for example, in case of a cup type of vessel, since the liquid passage is inserted by a mechanical operation during the liquid discharge operation, only the insertion portion thereof may be constructed with a metallic member or the like, and the remaining portions may be constructed with a highly flexible plastic member of a rubber member.

The presence or absence of the discharged liquid at an optional area can be measured by utilizing, for example, electric characteristics such as an electric conductivity of the liquid, or optical characteristics such as an absorbance of the liquid. For example, in case of the utilization of the electric conductivity, it is possible to determine the presence or absence of the liquid in such a way that two electrodes are placed by each other at a distance of several millimeters, an AC voltage or a DC voltage is applied between those electrodes, and the variation of an amount of the current flowing through the electrodes is measured. Further, in case of the utilization of the optical characteristics, it is possible to determine the presence or absence of the liquid in such a way that an optional area of the liquid passage is formed with an optical transparence or a semitransparence, a light source 3 and a photodetector element 1 are placed each on the opposite sides of the passage so that they are facing each other through the liquid passage, and the change of a refraction index and a transmission factor of the light are measured. Specifically, in a case where the discharged liquid contains a photoabsorption substance and/or an emission substance, it is possible to optically measure those substances. In case of the optical measurement, if the light source 3 and said photodetector element 1 are installed in such a way that a center of the optical axis coupling the light source and the photodetector element is given with an eccentricity with respect to a center of the liquid passage, the refractive index will be varied even if there is no absorption due to the liquid. Thus, it is possible to enhance the difference in a measuring result between a case where the liquid exists on the optical axis and a case where no liquid exists on the optical axis. It is especially preferable to employ such a structure in case of the optical measurement according to the present invention.

As apparent from the above-mentioned description, according to the present invention, it is possible to treat the measurement result concerning the presence or absence of the discharged liquid at an optional area of the liquid passage in the form of the output signals from the electrodes or the optical elements used for the measurement.

The measurement concerning the presence or absence of the discharged liquid on the liquid passage may be preferably adapted to be performed at an optional area of the liquid passage. It is sufficient for this area to be determined in such a manner that the measurement result can provide distinction between an implementation of a reliable discharge of the liquid and non-implementation. In general, the optional area may preferably be adapted to be set in such a range that the electric characteristics and the optical characteristics of the liquid can be measured, and at a position which is not so far from an aperture to introduce the liquid to be discharged to the passage. Specifically, it is preferable to set the optional area in such a manner that the time required for arrival of the discharged liquid from the aperture at the optional area is less than the time required for the liquid discharge operation. In a case where a liquid discharge apparatus according to the present invention is used in an automatic immunoassay apparatus or the like, and the continuous liquid discharge operation is performed, it is preferable to set the optional area near the liquid discharge outlet so that a monitor operation can be terminated within the time required for a discharge of the liquid.

The optional area may be constructed, if necessary, for measurement of the presence of absence of the discharged liquid, with a configuration different from other portions. For example, in a case where a measurement or detection is performed utilizing optical characteristics, it may be so arranged that if the discharge passage is constructed with a metallic member or an optically opaque member, only the optional area is constructed with an optically transparent or semitransparent member, and also with a square pole like configuration so as to efficiently utilize the light from a light source. Further, it may be so arranged that only the optical area is elongated to so as to be distinguishable of bubbles as much as possible, and on the contrary is thickened so as to install electrodes or the like thereon.

According to an embodiment of the present invention, the measurement of the presence or absence of the liquid discharged at an optional area of the liquid passage is implemented after a predetermined time elapses since the discharge operation for the liquid is initiated. It is assumed that an occurrence of clogging on the liquid passage in mid course of the operation stops the liquid flow at an arbitrary area of the liquid passage. Hence, if the presence of the liquid is detected after a predetermined time elapsed, that is, after the lapse of time which is deemed to be required for completion of the liquid discharge operation, then it may be determined that the liquid discharge operation is defective. According to this measurement, however, it may be estimated that an occurrence of clogging on the liquid passage at an initial stage of the discharge operation prevents the discharged liquid from arriving at the optional area, and as a result an presence of the liquid is not detected. Consequently, it is preferable to perform the measurement of the presence or absence of the liquid discharged at the optional area at least two times, that is, when the discharged liquid passes through the optional area, and after passing through that area. According to such a measurement, there is no need to especially provide a comparison operation, since a measurement result, which is to be obtained when the discharge operation has been normally implemented, is expected as matter of course.

As a method of the measurement with a single operation, it is exemplified that the measured is made of the lapse time required until obtaining a continuous measurement of the absence of the liquid after the presence of the liquid is first detected at an optional area since the liquid discharge operation is initiated. If no measurement value obtained, it is supposed that a clogging on the liquid passage occurs at a first stage of the discharge operation. If the obtained measurement value is larger than a normal value, it is supposed that a clogging on the liquid passage occurs at middle or later stages of the discharge operation, or a clogging on a part of the liquid passage occurs.

In a plurality of number of times of implementation of a measurement of the presence or absence of a liquid discharged at the optional area, it is possible to obtain a two dimensional result representative of a relation shown by an axis of abscissa denoting the time elapse since the discharge operation is initiated and a vertical axis denoting outputs of the electrodes or the optical elements involved in the measurement of the presence or absence of a liquid discharged. According to the present invention, it may preferably be adapted to provide such a process that the outputs involved in the measurement result are subjected to an arithmetic processing so that the measurement result can be obtained in the form of a two dimensional result, and the obtained result is compared with a corresponding result which will be obtained when the liquid discharge operation is normally completed.

By the way, the measurement result as to the presence or absence of a liquid will be output in the form of an analog signal from the electrodes or optical elements used in the measurement. Hence, it happens that the stain or a droplet sticking on the electrodes or optical elements causes a signal intensity to continuously vary independently of the presence or absence of a liquid. In order to remove the effect of such a noise, the output signal from the electrodes or optical elements is compared with a predetermined value or a threshold, and it is preferable to assume that the liquid is present only when the output signal exceeds the threshold. Hereinafter, the output signal, which has been subjected to such a comparison with the threshold, will be referred to as a digital output signal. The representation of a relation between time and the presence/absence with such a digital signal renders a comparison operation more easy, and is preferable.

In a case where a measurement according to the present invention is carried out a plurality of number of times, it is preferable to measure an integrated value of time during which the presence or absence of a liquid at an optional area is measured. More specifically, it is exemplified that the integrated value of time while liquid is present until the predetermined time is over since the presence of a liquid is first detected after the discharge operation is initiated. For example, in a case where there is fear such that the absence of a liquid is intermittently measured, such as in a case where bubbles pass through the optional area, it is sufficient to replace the measurement result indicating the intermittent presence of the liquid by a result indicating the presence of the liquid, or to set up a threshold so as to cancel the measurement result.

For determining whether the liquid discharge operation has adequately been performed, on the basis of the above-mentioned measurement result or the output signal representative of the measurement result, basically, it is sufficient to compare the obtained measurement result with a reference measurement result or the corresponding output signal which ought to be obtained when the discharge operation has adequately been performed. It is especially preferable that the reference measurement result has been obtained through an implementation regarding a liquid which has the same or similar characteristics as the liquid to be discharged.

For finally determining whether the liquid discharge operation has adequately been performed, it is sufficient that upon completion of the above-mentioned comparing operation, the determination is made, for example, in such a manner that if difference between the both results exceeds a predetermined value, the operation is determined to be incomplete or defective. It is possible to easily implement this determination by means of combination use of a computer and an electronic circuit. Particularly, in the case of comparison of the two dimensional measurement results, it is possible to implement this sort of determination by means of a computer utilizing a neuro network, and also possible to perform the determination by an operator himself. The use of a computer etc. is preferable because it permits an easy implementation in providing an association of a measurement result with time utilizing an internal clock thereof. Further, regarding the indication of a determination result, it may preferably be adapted, for example, to display on a display screen the two dimensional measurement result as it is, or if a problem on the discharge operation occurs, it may preferably be adapted to employ such an indication scheme that the operator is informed of occurrence of the problem by a buzzer or the like.

The method of monitoring and the monitor apparatus according to embodiments of the present invention will be described in more detail referring to the accompanying drawings.

Figure 1B:
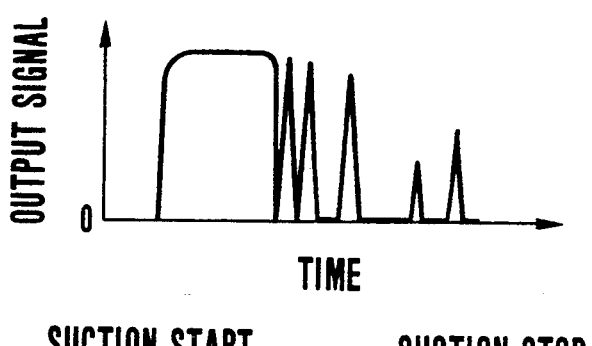

FIG. 1(a) and FIG. 1 (b) show measurement results on a two dimensional basis in a case where a discharge operation is satisfactorily performed, and particularly, FIG. 1 (a) is a graph in which a vertical axis shows an integrated value of time and an axis of abscissa shows time elapse since a liquid discharge operation is initiated. As apparent from FIG. 1(a), the integrated value rises after the initiation of the liquid discharge operation and becomes flat after a certain period of time elapse. FIG. 1(b) is a graph in which a vertical axis shows an output signal (not digital) from a liquid measuring unit and an axis of abscissa a time elapse since a liquid discharge operation is initiated. As seen from FIG. 1(b), while a liquid is continuously measured at the initial stage of the operation, the liquid is only intermittently measured the later stage of the operation. It is considered that the intermittent measurement result is caused by the fact that the bubbles or the like pass through the optional area.

Figure 2A:
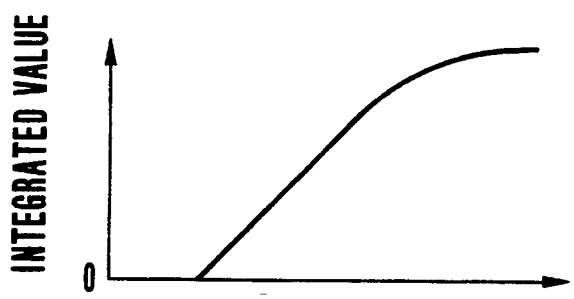
FIG. 2(a) and FIG. 2(b) show measurement results on a two dimensional basis in a case where the discharge operation is slightly defective, and particularly.
Figure 2B:
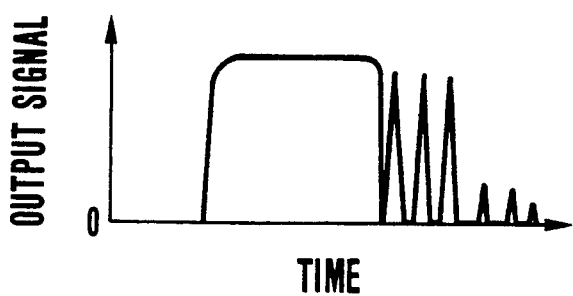

FIG. 2(a) and 2(b) to FIGS. 7(a) and (b) show measurement results in a case where the discharge operation is defective, which malfunction is brought by artificially producing the closing of the liquid passage such as clogging, and placing the liquid suction force generator and the like into disorder. Particularly, FIG. 2(a) and FIG. 2(b) are graphs showing the corresponding matters as in FIG. 1(a) and FIG. 1(b), respectively, and FIGS. 3(a) and 3(b) to FIGS. 7(a) and (b) as well.

From FIG. 2(a) and FIG. 2(b), in comparison with FIG. 1(a) and FIG. 1(b), respectively, it would be understood that there are found differences in the points such as an integrated value at the saturation point of time, the time required for the saturation, and duration of a signal indicating the presence of the liquid, all of which items take values larger than those in FIG. 1(a) and FIG. 1(b), respectively. In this manner, it is possible to identify a malfunction of the operation through the comparison with FIGS. 1(a) and 1(b).

Figure 3A:
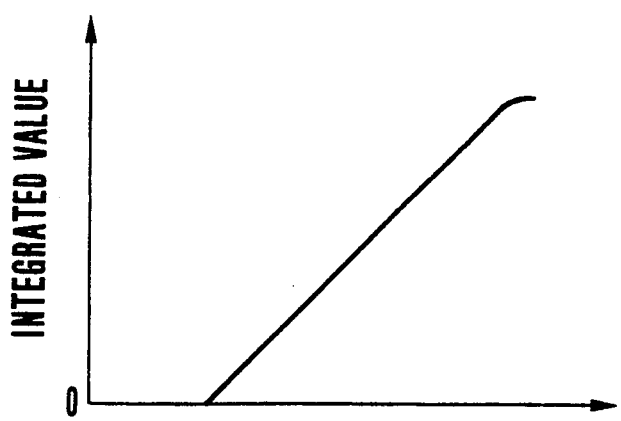
FIG. 3(a) and FIG. 3(b) show measurement results on a two dimensional basis in a case where the discharge operation is defective, and particularly.
Figure 3B:
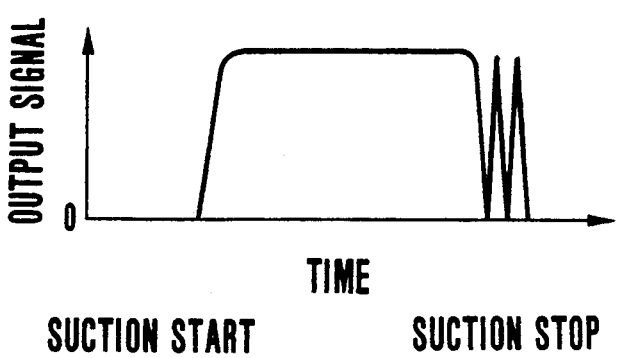

From FIG. 3(a) and FIG. 3(b), in comparison with FIG. 1(a) and FIG. 1(b), respectively, it would be understood that there are found differences in the points such that the graph of FIG. 3(a) shows no saturation within a predetermined time, and that duration of a signal indicating the presence of the liquid is longer than that in FIG. 1(b). Thus, it is possible to identify a malfunction of the operation through the comparison with FIGS. 1(a) and 1(b).

Figure 4A:
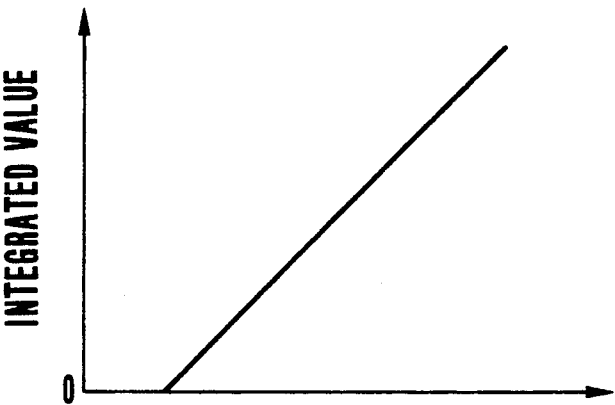
FIG. 4(a) and FIG. 4(b) show measurement results on a two dimensional basis in a case where the discharge operation is defective, and particularly.
Figure 4B:
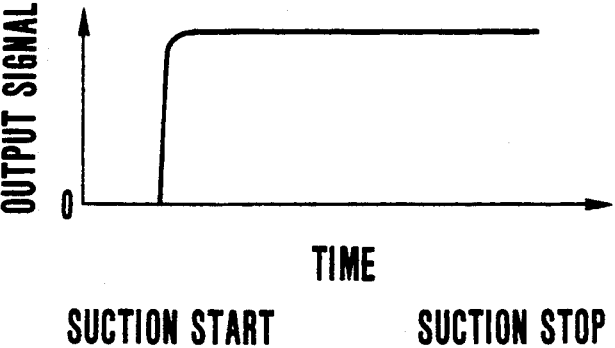

From FIG. 4 (a) and FIG. 4 (b), in comparison with FIG. 1(a) and FIG. 1(b), respectively, it would be understood that there are found differences in the points such that the graph of FIG. 4(a) shows no saturation within a predetermined time, and that duration of a signal indicating the presence of the liquid is longer than that in FIG. 1(b). Thus, it is possible to identify a malfunction of the operation through the comparison with FIGS. 1(a) and 1(b).

Figure 5A:
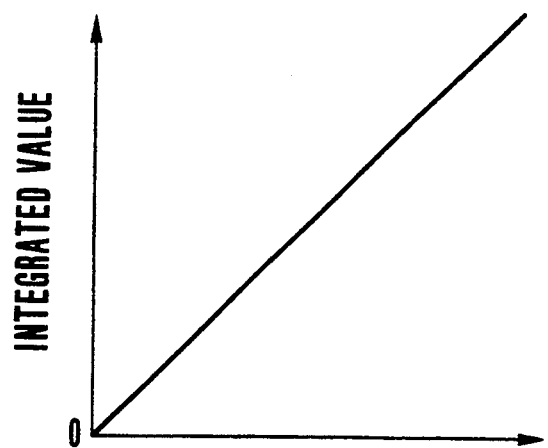
FIG. 5(a) and FIG. 5(b) show measurement results on a two dimensional basis in a case where the discharge operation is defective, and particularly.
Figure 5B:
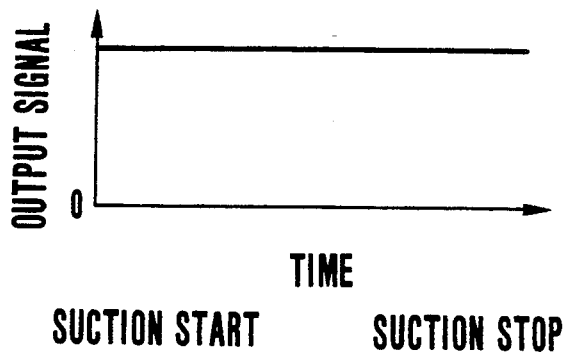

From FIG. 5(a) and FIG. 5(b), in comparison with FIG. 1(a) and FIG. 1(b), respectively, it would be understood that there are found differences in the points such that the graph of FIG. 5(a) shows a rising at an initial point of the discharge operation and no saturation within a predetermined time, and that FIG. 5(b) shows a measurement of a signal indicating the presence of the liquid from the first, but no measurement of a signal indicating the absence of the liquid. Thus, it is possible to identify a malfunction of the operation through the comparison with FIGS. 1(a) and 1(b). The measurement of the presence of the liquid from the first in FIG. 5(b) may be interpreted as such that the liquid, which ought to be discharged in the previous operation, had remained at any optional area.

Figure 6A:
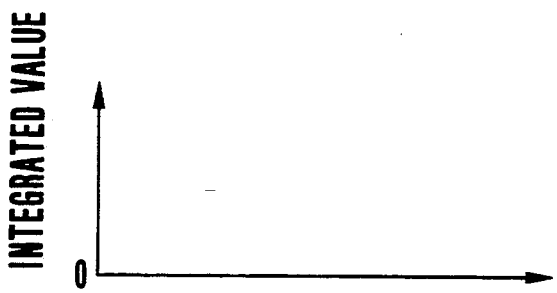
FIG. 6(a) and FIG. 6(b) show measurement results on a two dimensional basis in a case where the discharge operation is defective, and particularly.
Figure 6B:
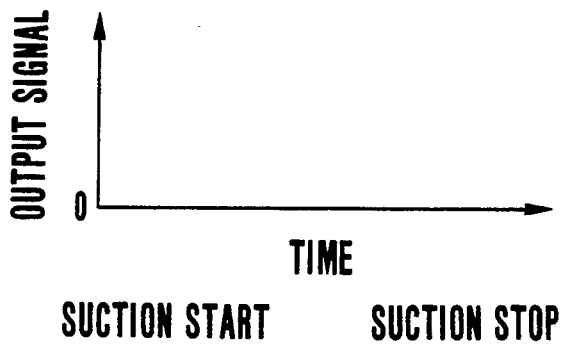

From FIG. 6(a) and FIG. 6(b), in comparison with FIG. 1(a) and FIG. 1(b), respectively, it would be understood that there are found differences in the points such that the graphs of FIG. 6(a) and FIG. 6(b) show no appearance of any values and signals, respectively, that is, the presence of the liquid is not measured. Thus, it is possible to identify a malfunction of the operation through the comparison with FIGS. 1(a) and 1(b). The graphs of FIG. 6(a) and FIG. 6(b) showing no appearance of any values and signals may be interpreted as such that an opening for liquid discharge is completely clogged from the first, or the opening is not in contact with the liquid in the vessel.

Figure 7A:
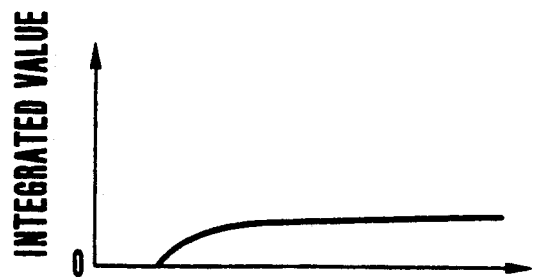
FIG. 7(a) and FIG. 7(b) show measurement results on a two dimensional basis in a case where the discharge operation is defective, and particularly.
Figure 7B:
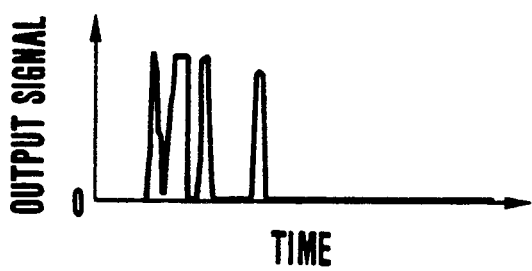

From FIG. 7(a) and FIG. 7(b), in comparison with FIG. 1(a) and FIG. 1(b), respectively, it would be understood that there are found differences in the points such as an integrated value at the saturation point of time, the time required for the saturation, and duration of a signal indicating the presence of the liquid, all of which items take values smaller than those in FIG. 1(a) and FIG. 1(b), respectively.

Figure 8:
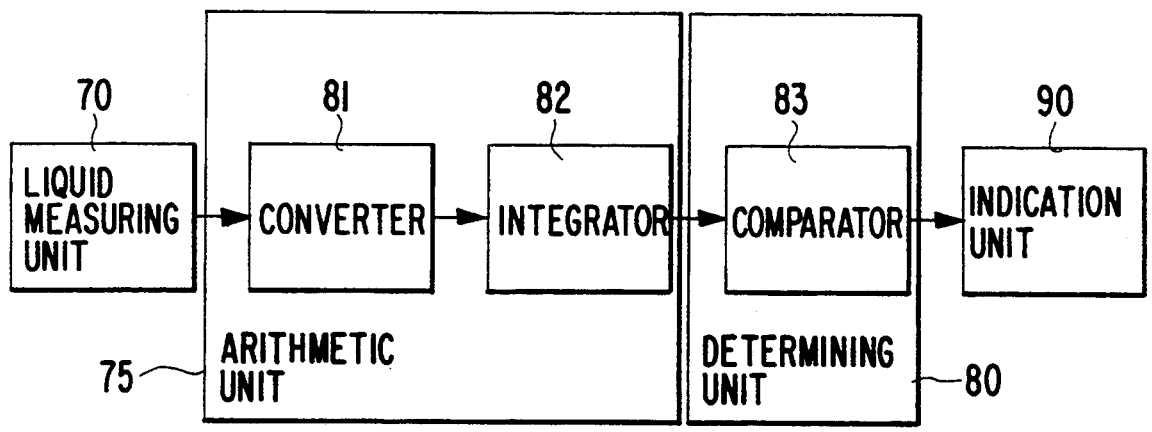
FIG. 8 is a block diagram schematically showing a structure of a determining unit according to an embodiment of an arithmetic unit and the present invention.

FIG. 8 is a block diagram schematically showing a structure of an arithmetic unit determining unit 80 according to an embodiment of the present invention. In FIG. 8, a liquid measuring unit 70 provided on a liquid passage is adapted for measuring the presence or absence of a liquid discharged at an optional area of said liquid passage, and for outputting a signal correlated with a measurement result. The arithmetic unit 75 and the determining unit 80 are adapted for storing a reference output signal from the liquid measuring unit 70, which is to be obtained when the discharge of the liquid is reliably or satisfactorily carried out, and for comparing it with an output signal from the liquid measuring unit 70, which is obtained during a liquid discharge operation through a monitor, thereby determining whether the liquid discharge operation is reliably or satisfactorily carried out. The signal outputted from the liquid measuring unit is correlated with a measurement result, and applicable are any of signals which are produced, for example, either when the liquid is present or absent.

In FIG. 8, the arithmetic unit 75 comprises a converter 81 for digitalizing an output signal (measurement value) from the liquid measuring unit 70, an integrator 82 for integrating the digitalized signal from the converter 81, and the determining unit 80 comprises a comparator 83 for comparing an integrated value (detection pattern) from the integrator with a reference value which will be formed by means of similar processing of an output signal produced from the liquid measuring unit when the liquid discharge is satisfactorily carried out and for determining on the basis of a comparison result whether the liquid discharge operation is satisfactorily carried out. The arithmetic unit/determining unit is provided with memory (not illustrated) for storing the output signal produced from the liquid measuring unit when the liquid discharge is satisfactorily carried out.

Figure 9:
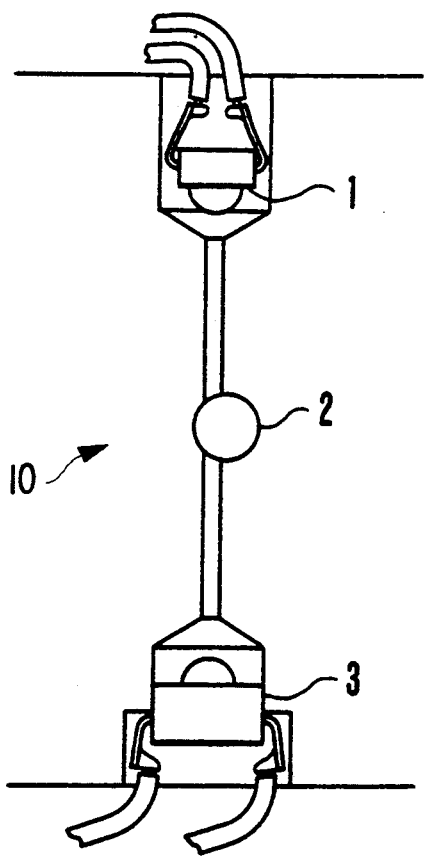
FIG. 9 is a sectional view of a structure of a measuring unit according to an embodiment of the present invention.

FIG. 9 shows a section of a measuring unit for measuring the presence or absence of a liquid on an optional area of a liquid passage constituted with a transparent or semi-transparent tube, utilizing optical characteristics of the liquid. Shown with a circle at the center is a section of the liquid passage 2. An infrared light emitting diode 3 as a light source and a phototransistor 1 as a photosensitive element are placed on the opposite sides of the liquid passage so that they are facing each other through the liquid passage. According to the structure of the measuring unit as shown in FIG. 9, the infrared light emitting diode 3 and the phototransistor 1 are installed in such a way that a center of the optical axis coupling those elements is given with an eccentricity with respect to a center of the liquid passage.

The present invention will be described more in detail in reference to examples of a liquid discharge apparatus according to the present invention which is manufactured as a B/F washing device for an immunoassay apparatus and results of a discharge operation using the liquid discharge apparatus will be described.

Example 1 A liquid discharge apparatus built as a B/F washing apparatus for an immunoassay apparatus.

Figure 10:
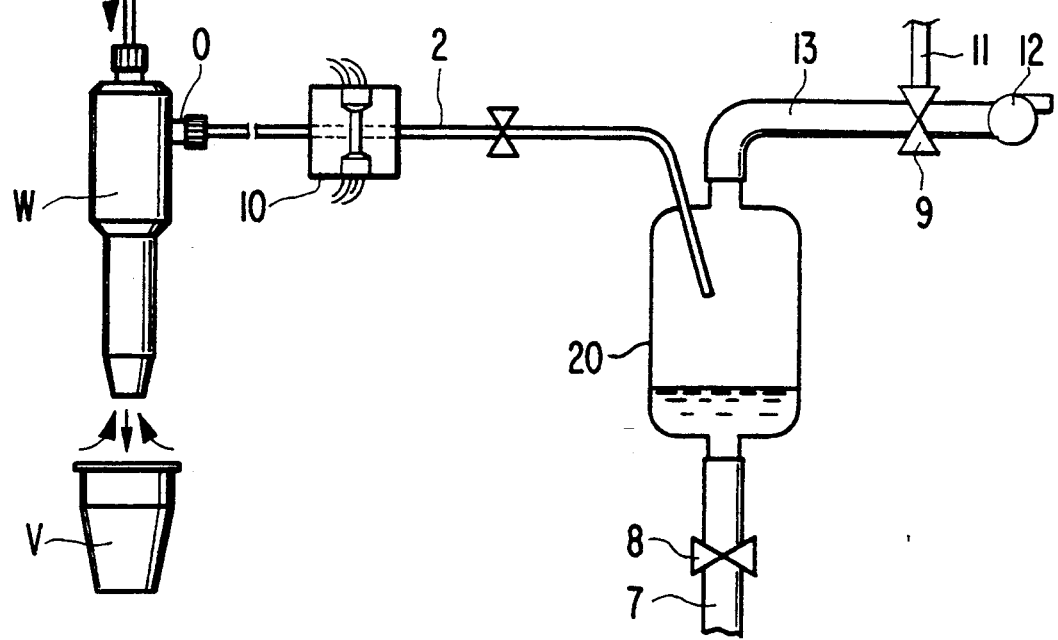
FIG. 10 illustrates a monitor apparatus according to the present invention, which is built as a part of a washing apparatus involved in an immunoassay, as constructed in accordance with Example 1.

FIG. 10 illustrates a liquid discharge monitor apparatus according to the present invention, which is built as apart of a B/F washing apparatus involved in a heterogeneous immunoassay apparatus, as constructed in accordance with Example 1. It is necessary for the B/F washing apparatus for the heterogeneous immunoassay apparatus to discharge or exhaust a liquid in a vessel V and to wash the vessel V and the solid phase. Consequently, according to Example 1, a passage for washing solution supply is constituted with a tube configuration of plastic member, and outside thereof the similar member is fitted to form a B/F washing apparatus W consisting of an inside-outside double tube. A space defined by the inside of the outer tube and the outside of the inner tube forms a liquid passage according to the present invention, and the inside of the inner tube serves as the passage for washing solution supply.

The passage 2 for washing solution supply is connected to a liquid pool filled with the washing solution, from which liquid pool the washing solution is ejected by means of operations of a pump 12. The space define by the inside of the outer tube and the outside of the inner tube, which forms the liquid passage according to the present invention, is finally connected to a vacuum tube 13 and also to a trap bottle 20 for the discharged liquid, which bottle is maintained at an atmosphere of −0.5 atm. The trap bottle is used to prevent the discharged liquid from reaching the vacuum tube 13, and is connected to a drain pipe 7 through a valve 8 for the purpose of a liquid drain. The inner tube and the trap bottle 20 are coupled with each other through an inside diameter 1.6 mm of semi-transparent TEFLON tube having a flexibility, and in mid course there are a liquid measuring unit 10 as a part of the apparatus according to the present invention and a valve 9 for releasing pressure in the liquid passage and the trap bottle to an atmospheric pressure as at 11. As the liquid measuring unit 10, the one as shown in FIG. 9 is applicable. Such a liquid measuring unit is electrically connected to an arithmetic unit determining unit as shown in FIG. 8 or the like.

The carrier for the heterogeneous immunoassay is one chosen in the range of 1.3 mm to 1.5 mm in the diameter. Such a carrier enters a vessel of which the inside diameter is 10 mm and the capacity is 1 ml. Consequently, the outer tube of the B/F washing apparatus W as the top of the liquid passage is given with the outside diameter: 6 mm, the inside diameter: 2.4 mm, while the inner tube is given with the outside diameter: 1.4 mm, so that the liquid passage, which is defined by the inside of the outer tube and the outside of the inner tube, prevents the carrier from passing therethrough. The B/F washing apparatus W is fixed on a frame (not illustrated) which is movable up and down in a vertical line. In operation, the frame is moved up and down in such a manner that a discharge opening on an edge portion travels downward to the bottom of the vessel V, so that about 700 μl of liquid in the vessel can be discharged.

Figure 11:
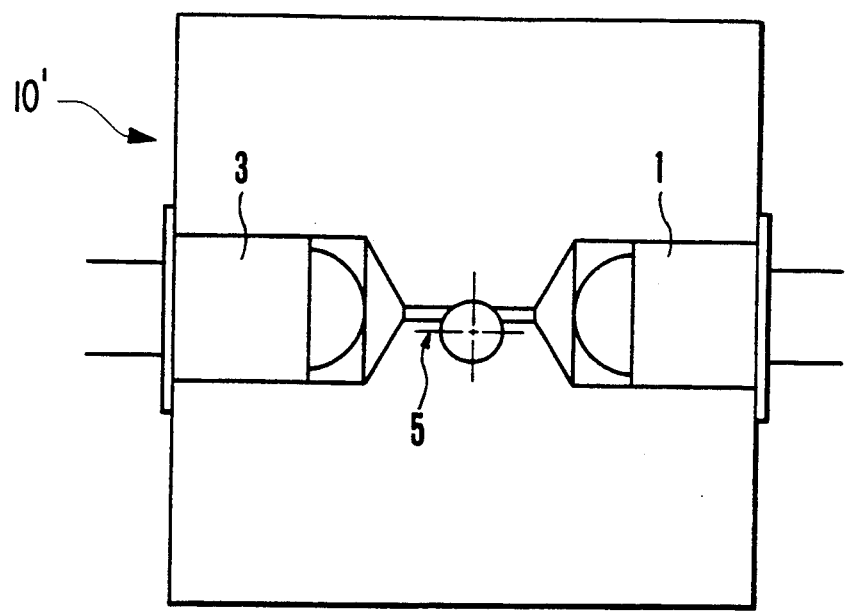
FIG. 11 illustrated a liquid measuring unit in a monitor apparatus constructed in accordance with Example 1.

FIG. 11 illustrates a liquid measuring unit 10' similar to that shown in FIG. 9, in which an infrared light emitting diode 3 (TLN101A, by Toshiba ) as a light source and a phototransistor 1 (TPS601A, by Toshiba) as a photosensitive element are placed each other on the opposite sides of a teflon tube of the outside diameter: 2.1 mm, the inside diameter: 1.5 mm in the sectional direction of the liquid passage so that they are facing each other through the liquid passage. Between those elements, there is provided a slit 5 dimension 0.5×4 mm) configuration of aperture adapted to permit a beam of the light source to pass through, which aperture penetrates through the plastic member. According to the structure of the measuring unit as shown in FIG. 11, the infrared light emitting diode 3 and the phototransistor 1 are installed in such a way that the center of optical axis coupling those elements is given with an eccentricity with respect to a sectional center of the liquid passage. An eccentric distance between these centers is 0.65 mm. The use of the slit 5 makes it possible to enhance directivity of the light to be able to reach the phototransistor 1. Further, the arrangement of the measuring unit, in which the center of optical axis coupling both the elements is given with an eccentricity with respect to a sectional center of the liquid passage, makes it possible, for instance even if a fine droplet traverses the optical axis, to avoid the direct influence of such a droplet. Thus, it is possible to provide a small threshold for the determining unit, and then to cope with a subtle variation in a measurement result.

Figure 12:
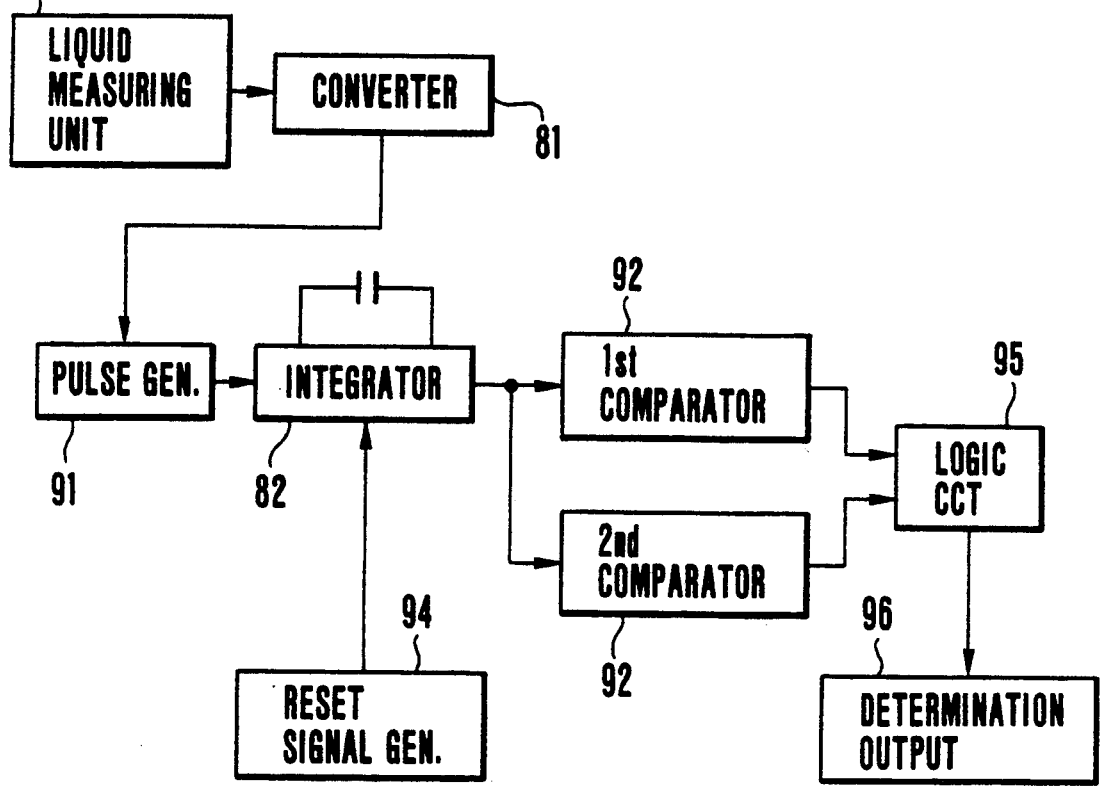
FIG. 12 is a block diagram schematically showing an arrangement of a liquid measuring unit and a determining unit in a monitor apparatus constructed in accordance with Example 1.

FIG. 12 is a block diagram schematically showing an arrangement of a liquid measuring unit, arithmetic unit and a determining unit in a monitor apparatus constructed in accordance with Example 1. An output from the liquid measurement unit 70 is applied to a converter 81. The converter 81 compares the output from the liquid measuring unit 70 with a threshold entered from an input device (not illustrated) to provide a digitalization. In comparison, when an input signal from the liquid measuring unit 70 exceeds the threshold, the converter 81 instructs a pulse generator 91 to generate a pulse, and on the other hand, when the input signal from the liquid measuring unit 70 does not exceed the threshold, the converter 81 generates no such instruction. This arrangement is intended to generate digital signals eliminating noises which will be generated, for example, when bubbles or the like pass through the optional area. According to the present embodiment, the threshold is chosen at 10 volt which is deemed to be sufficient to eliminate the noise.

The pulse generator 91 is adapted to generate 3 kHz of pulses in response to the instruction from the converter 81. The pulses output from the pulse generator are integrated by an analog integrator 82 employing a capacitor or a pulse counter. The pulse generator 91 would be omitted when the pulse is integrated by an analog integrator. In the apparatus according to the present embodiment constructed as the B/F washing apparatus, the integrator 82 is provided with a reset circuit so that the B/F washing is repeatedly carried out. According to the present embodiment, at the time point that the liquid discharge opening is disconnected from the vessel by elevating the frame after the discharge operation for the liquid, a reset signal is generated from a reset signal generator 94 to reset the integrator 82 so that electric charge of the capacitor is discharged.

It can be supposed that an output signal of the integrator 82 will take a predetermined range of value, if the liquid discharge is satisfactorily performed. Thus, according to the present embodiment, the output signal of the integrator 82 is compared with reference values by means of a comparator comprising a first comparator circuit 92 and a second comparator circuit 93, which reference values each correspond to the predetermined range of value of the output signal of the integrator 82 that is obtained when the liquid discharge is satisfactorily performed, and have been stored in a memory (not illustrated). As a result of the comparison, if it is determined that the output signal of the integrator 82 is out of a predetermined range of value, an determination output 96 is generated through a logic circuit 95 to an indication unit 90 (see FIG. 8) so as to ring the buzzer to inform an operator of an occurrence of a trouble on the liquid discharge operation. It is possible to modify the predetermined range of value of the output signal of the integrator 82 that is obtained when the liquid discharge is satisfactorily performed, by means of entry through an input device (not illustrated).

Example 2 B/F washing using a liquid discharge apparatus built as a B/F washing apparatus for an immunoassay apparatus.

A liquid discharge operation has been performed, using the B/F washing apparatus described in Example 1, on the vessel containing 700 μl.

Figures 13A, 13B:
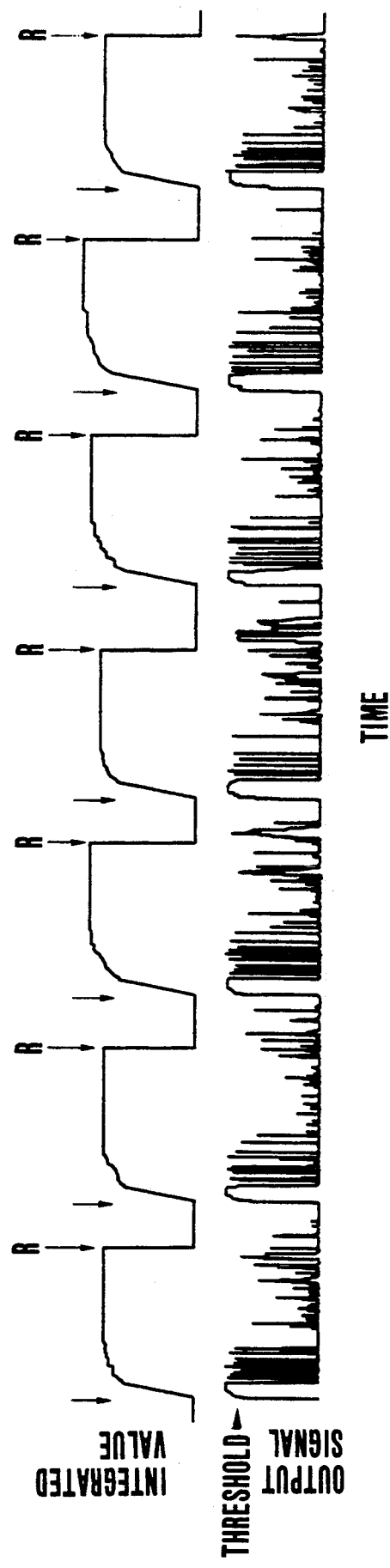
FIG. 13(A) and FIG. 13(B) are charts plotting an output signal of a liquid measuring unit (graph shown in part (A) of FIG. 13) and an output signal of an integrator (graph shown in part (B) of FIG. 13), in the event that a liquid discharge operation is actually monitored in accordance with Example 2, in which axis of abscissa denotes time elapsed, simple arrows denote time points where a B/F separation nozzle goes down, and arrows marked with a symbol R denote time points at where a B/F separation nozzle rises, and at when integrator is reset respectively. In accordance with the chart of FIG. 13, the liquid discharge operation is performed seven times.

FIG. 13 is a chart plotting an output signal of a liquid measuring unit (graph shown in part (B) of FIG. 13) and an output signal of an integrator (graph shown in part (A) of FIG. 13), in the event that a liquid discharge operation is satisfactorily performed in accordance with Example 2, in which the axis of abscissa denotes time elapse, simple arrows denote time points at which a B/F separation nozzle goes down, and arrows each marked with a symbol R denote time points at which a B/F separation nozzle rises, respectively. In accordance with the chart of FIG. 13, the liquid discharge operation is performed seven times. The arrow marked with symbol R also indicates that the discharge operation is once completed, and the reset circuit of the integrator is operated with the elevation of the liquid discharge outlet for the subsequent operation, so that the electric charge of the capacity is reset or discharged. The arrow in part (B) of FIG. 13.denotes the threshold which is given with 10 volt. Among the spike-like peaks appearing on the output signal of the liquid measuring unit shown in part (B) of FIG. 13, the relatively higher ones of the output have been observed when the discharged liquid passes through the optional area of the liquid passage in a condition such that the discharged liquid is bubbled, and the relatively lower ones of the output have been observed when the discharged liquid passes through the optional area of the liquid passage in a condition such that the discharged liquid is of a droplet like.

Those noises have been suppressed or eliminated in the output of the integrator. Thus, the output of the integrator provides a preferable state for comparison with a measurement result obtained when the operation is satisfactorily performed. That is, the integrating processing of the out put signal of the liquid measuring unit renders an age-based presence pattern of the discharged liquid more clear. From the present embodiment, it would be understood that the integrated value output of the integrator is less than the integrated value for time during which an aperture for liquid discharge goes down.

FIG. 14 is a chart plotting an output signal of a liquid measuring unit (graph shown in part (A) of FIG. 14) in the event that a liquid discharge operation is reliably or satisfactorily performed and an output signal of the liquid measuring unit (graph shown in part (B) of FIG. 14) in the event that a liquid discharge operation is defective, in which axis of abscissa denotes time elapsed. The result in a case where a liquid discharge operation is defective has been obtained through a measurement by means of artificial closing of the aperture for discharge by about half of the area thereof. In accordance with the chart of FIG. 14, when the liquid discharge operation is performed ten times, it is treated as one set, and five sets of result are shown in the respective events. An initial operation of the respective sets is marked with an arrow. The reason why there appear larger width of measurement results for the tenth time on the respective sets is that an operation for the replacement of the vessel was performed before the operation on each set.

In a case where about half of the area of the aperture for discharge is closed (part (B) of FIG. 14), there appears relatively a higher amplitude of output signal. The reason why there appears a relatively higher amplitude of output signal is that the discharge operation for the liquid takes time and existence time of the discharged liquid at the optional area becomes long (the measurement result is the integrated value of the time, and thus it takes a larger integrated value). Thus, it is possible to accurately monitor the operational defective by means of comparison with a case where the discharge operation is satisfactorily performed. According to the present embodiment, assuming that an output (integrated value) of the integrator, which is obtained when the liquid discharge operation has been satisfactorily performed, is smaller than the integrated value of time is less than the integrated value for time during which an aperture for liquid discharge goes down, there is so arranged that such an integrated value enters the determining unit, so that the buzzer rings if the liquid discharge operation is defective. In this circumstance, in the event that about half of the area of the aperture for discharge was closed (part (B) of FIG. 14), the buzzer ringed once in every 60 times of operation.

According to the method of monitor for a liquid discharge, in a case where the discharge operation is defective, for example, owing to the fact that the liquid to be discharged out of the vessel remains in the vessel or the discharge passage, it is possible to detect such defectiveness of the operation. Further, in a case where both the liquid discharge and the washing solution supply are performed for an immunossay reaction or the like, the stop of supplying operation for the washing solution on the basis of a monitor result makes it possible to avoid such a danger that the liquid overflows the vessel.

Thus, according to the present invention, there is no need to regularly perform an inspection of a liquid discharge apparatus to keep it at a reliable state so that a discharge operation for a liquid is kept at a good state. Further, according to the present invention, there is no need to cope with unexpected situations in such a way that even if the apparatus is in a good condition, parts used for a given period of time or a given number of times are replaced by new parts. Consequently, it is sufficient in the present invention to implement the inspection or the replacement or substitution of the parts only when the incomplete operation is monitored.

Therefore, according to the present invention, it is possible to provide measurement apparatuses and the like which are excellent in respect to safety, maintenance and inspection, and also capable of implementing a high reliability of measurement and the like.

What is claimed is:

1. A method of monitoring discharge of a liquid, comprising the steps of:
   measuring a presence or absence of the liquid discharged at an optional area of a passage for the liquid during discharging of the liquid from a vessel through the passage;
   comparing a measurement result obtained in said measuring step with a reference measurement result which is obtained when discharge of the liquid is reliably carried out; and
   determining whether a discharge operation for the liquid has been reliably performed.

2. A method according to claim 1, wherein the measurement in said measuring step is implemented by once after a predetermined time elapse since the discharge operation for the liquid is initiated.

3. A method according to claim 1, wherein the measurement in said measuring step is implemented a plurality of number of times during a predetermined time elapse since the discharge operation for the liquid is initiated, and a relation between time and the presence or absence of the discharged liquid is measured.

4. A method according to claim 3, wherein a measurement result as to the relation between time and the presence or absence of the discharged liquid is representative of time required until obtaining a continuous measurement of the absence of the liquid.

5. A method according to claim 3, wherein a measurement result as to the relation between time and the presence or absence of the discharged liquid is representative of an integrated value of time as to the presence of the liquid or an integrated value of time as to the absence of the liquid.

6. An apparatus for monitoring a discharge of a liquid comprising:

a liquid passage for forming a discharge outlet for the liquid, at least one end of the liquid passage being connected directly or indirectly to liquid suction force generator means, and another end thereof being connected to a vessel; and liquid measuring means provided on said liquid passage for measuring presence or absence of the liquid discharged at an optional area of said liquid passage.

7. An apparatus according to claim 6, further comprising an arithmetic unit for causing an output signal from said liquid measuring means related to the presence or absence of the liquid to be associated with time elapsed.

8. An apparatus according to claims 6 or 7, further comprising a determining unit for storing a reference output signal from said liquid measuring means or a reference output signal from said arithmetic unit, which are to be obtained when the discharge of the liquid is reliably carried out, and for comparing those with an output signal from said liquid measuring means or an output signal from said arithmetic unit, which are obtained during a liquid discharge operation.

9. An apparatus according to any of claims 6 or 7, further comprising an indication unit for indicating an output signal from said liquid measuring means, said arithmetic unit or said determining unit.

10. An apparatus according to any of claims 6 or 7, wherein said liquid measuring means comprises a light source and a photodetector element, which are placed on the opposite sides of said liquid passage so that they are facing each other through said liquid passage.

11. An apparatus according to claim 10, wherein said light source and said photodetector element are installed in such a way that a center of optical axis coupling said light source and said photodetector element is positioned eccentrically with respect to a center of said liquid passage.

12. An apparatus according to claim 8, further comprising an indication unit for indicating an output signal from said liquid measuring means, said arithmetic unit or said determining unit.

13. An apparatus according to claim 8, wherein said liquid measuring means comprises a light source and a photodetector element, which are placed on the opposite sides of said liquid passage so that they are facing each other through said liquid passage.

14. An apparatus according to claim 9, wherein said liquid measuring means comprises a light source and a photodetector element, which are placed on the opposite sides of said liquid passage so that they are facing each other through said liquid passage.

15. An apparatus according to claim 13, wherein said light source and said photodetector element are installed in such a way that a center of optical axis coupling said light source and said photodetector element is positioned eccentrically with respect to a center of said liquid passage.

16. An apparatus according to claim 14, wherein said light source and said photodetector element are installed in such a way that a center of optical axis coupling said light source and said photodetector element is positioned eccentrically with respect to a center of said liquid passage.

* * * * *